United States Patent [19]
Block et al.

[11] Patent Number: 4,604,480
[45] Date of Patent: Aug. 5, 1986

[54] METHOD FOR THE PREPARATION OF SULFONES AND COMPOUNDS CONTAINING CARBON CHAINS HAVING CONJUGATED UNSATURATION AND THE COMPOUNDS RESULTING FROM SUCH METHOD

[75] Inventors: Eric Block, Delmar; Mohammad Aslam, Menands, both of N.Y.

[73] Assignee: The Research Foundation of State University of New York, Albany, N.Y.

[21] Appl. No.: 523,276

[22] Filed: Aug. 15, 1983

[51] Int. Cl.$^4$ ............... C07F 7/04; C07C 2/76
[52] U.S. Cl. .................. 556/445; 556/449; 556/465; 556/487; 585/534; 585/601; 585/357; 568/626; 568/667; 568/687; 568/700; 568/843; 570/135; 570/136; 570/189; 570/217; 570/226; 204/157.79
[58] Field of Search .......... 585/515, 526, 601; 568/28, 35; 556/445

[56] References Cited
U.S. PATENT DOCUMENTS

| | | | |
|---|---|---|---|
| 2,502,431 | 4/1950 | Copenhaver et al. | 585/603 |
| 3,073,873 | 1/1963 | Franzus et al. | 585/603 |
| 3,441,614 | 4/1967 | Asscher et al. | 568/28 |
| 3,830,862 | 8/1974 | Meyer et al. | |
| 4,022,804 | 5/1977 | Boell | |

FOREIGN PATENT DOCUMENTS 1087879  10/1967  United Kingdom .......... 568/28

OTHER PUBLICATIONS

Paquette, Leo A., The Base-Induced Rearrangement of α-Halo Sulfones, *Accounts of Chemical Research*, vol. I (1968), pp. 209–212.
Chen et al., The Michael Induced Ramberg–Backlund Olefin Synthesis, *Tetrahedron*, 51 (1977) pp. 4527–4530.
Paquette, Leo A., The Ramberg–Backlund Rearrangement, *Organic Reactions*, 25 (1977) pp. 1–33, John Wiley & Sons.
Block, Eric, *Reactions of Organosulfur Compounds*, pp. 75–79, (1978), Academic Press.
Burger, J. J. et al., The Michael Induced Ramberg–Backlund Homologation to Conjugated Isoprenoids, *Tetrahedron*, 37 (1981), pp. 417–424.
Naf, Ferdinand et al., A Novel Synthesis of Linear Polyenes Via Conjugate Addition of Cuprates etc., *Tetrahedron* 23(48) (1982), pp. 5043–5046.
J.A.C.S., 1983, 105, pp. 6165–6167, Block et al.
J.A.C.S. 1983, 105 pp. 6164–6165, Block et al.

*Primary Examiner*—Joseph L. Schofer
*Assistant Examiner*—Peter F. Kulkosky
*Attorney, Agent, or Firm*—Howard M. Ellis; Michael L. Dunn

[57] ABSTRACT

A method for the preparation of a first sulfone compound of the formula:

$$X_1C_1SO_2R_a$$

with $R_1$ and $R_2$ as substituents on $C_1$, wherein $R_a$ is

H, $R_4$, $R_c$, $-C_2-C_3-C_4R_6$ $R_3$, $R_b$, $R_5$ where $R_b$ is Br and $R_c$ is H except that $R_b$ and $R_c$ together may be an electron pair when $R_6$ is a radical of the formula:

$R_7$, H $-C_5-C_6R_9$;

Br, $R_8$ wherein $X_1$ is independently chlorine, bromine or iodine and $R_1$ and $R_2$ are independently at each occurrence hydrogen or, substituted or unsubstituted, phenyl or alkyl where the substituents are halogen or alkoxy or additional $-SO_2Br$ groups; provided that, each carbon atom of $R_1$ or $R_2$ which contains $-SO_2Br$ also contains an $X_1$ group and wherein $R_3$ through $R_9$ are independently $-OZ, -C_6M_5, -Z, -SiZ_3$ or $-X_2$, where Z is hydrogen or substituted or unsubstituted phenyl, alkyl, alkenyl or alkynyl; $X_2$ is chlorine, bromine, iodine or fluorine; M is independently at each occurrence Z or $X_2$; $R_3$ and $R_4$ may together be an electron pair; two or more of $R_3$, $R_4$, $R_5$ and $R_6$ may be combined together and with one or more of $C_2$, $C_3$ or $C_4$ to form a ring structure and $R_1$ and $R_2$ may be joined together with $C_1$ to form a ring structure; said method comprising reacting a 1-haloalkyl 1-sulfonyl halide with a second compound of the formula:

H, $R_4$, $R_d$ $C_2=C_3-C_4R_{10}$ $R_3$, $R_5$ at a temperature below 25° C. for less than 12 hours where $R_3$, $R_4$ and $R_5$ are as previously described, $R_{10}$ is $R_6$ as previously described or $R_{11}$, a radical of the formula:

$R_7$, H $-C-CR_9$ $R_e$, $R_8$ where $R_7$, $R_8$ and $R_9$ are as previously described and $R_d$ is H or when $R_{10}$ is $R_{11}$ forms an electron pair with unshared electron $R_e$; provided that, none of $R_1$ through $R_{11}$ interfere with the reaction of said 1-haloalkyl 1-sulfonyl halide with said second compound; and provided that, elimination of two hydrogens, $X_1$, Br and $SO_2$ from said first compound will yield two additional non-aromatic conjugated carbon-carbon unsaturated bonds as a result of such elimination.

10 Claims, No Drawings

METHOD FOR THE PREPARATION OF SULFONES AND COMPOUNDS CONTAINING CARBON CHAINS HAVING CONJUGATED UNSATURATION AND THE COMPOUNDS RESULTING FROM SUCH METHOD

This invention was made with Government support under CHE 811530801 awarded by the National Science Foundation. The Government has certain rights in this invention.

BACKGROUND OF THE INVENTION

A. Field of the Invention

This invention relates to the preparation of sulfones and compounds containing carbon chains having conjugated unsaturation and more particularly relates to the preparation of such sulfones which contain halogen groups which can be eliminated in conjunction with hydrogen and $SO_2$ to yield a carbon chain having conjugated unsaturation.

B. History of the Prior Art

In the prior art, some compounds containing conjugated nonaromatic aliphatic unsaturated carbon-carbon bonds were readily prepared from petroleum feed stock. Unfortunately, only short chain compounds containing such conjugated bonds could be prepared in this way and more complex compounds were difficult to prepare or had not been prepared at all. Such compounds containing conjugated unsaturation are highly desirable for numerous reasons. In particular, such compounds can act as monomers for the preparation of polymeric materials having special properties, have utility in the manufacture of fragrances and as intermediates in the manufacture of numerous products such as fungicides, algicides, insect sex attractants and other biologically active compounds.

It has been known that certain aliphatically unsaturated compounds could be prepared by means of a reaction known as the Ramberg-Backlund reaction. In this reaction, a haloalkyl sulfone yields an olefin upon treatment with a base. Unfortunately, such haloalkyl sulfones have been difficult to prepare and, in general, do not yield compounds containing conjugated aliphatic unsaturation. Descriptions of the Ramberg-Backlund Reaction and some of the difficult methods for preparation of the intermediate sulfones are discussed in "The Ramberg-Backlund Rearrangement", Paquette, Organic Reactions, Vol. 25, Wiley & Sons (1977); "The Base-Induced Rearrangement of Alphahalosulfones"; Paquette; "Accounts of Chemical Research", Vol. 1, p. 209 (1968); "Reactions of Organosulfur Compounds", Eric Block, pp. 75–79, Academic Press (1978); "The Michael Induced Ramberg-Backlund Olefin Synthesis", Chen et al, Tetrahedron Letters, Issue 51, pp. 4527 (1977) and "The Michael Induced Ramberg-Backlund Homologation to Conjugated Isoprenoids", Berger et al, Tetrahedron, Vol. 37, pp. 417–424, (1981); and "A Novel Synthesis of Linear Polyenes via Conjugate Addition of Cuprates to Alpha, Beta, Gamma, Delta Di-unsaturated Sulfones followed by $SO_2$ Extrusion", Naff et al, Tetrahedron, Vol. 23, No. 48, pp. 5043–5046 (1982).

The primary problem in the prior art, with using the Ramberg-Backlund Reaction to obtain conjugated olefins, has been the preparation of appropriate sulfones which lend themselves to preparation of conjugated compounds. In the prior art, there has been no good single-step process for the preparation of such sulfones.

Examples of prior art references which deal with the preparation of sulfones which are subsequently treated to obtain some unsaturation but which unfortunately did not yield aliphatic conjugated unsaturation, are U.S. Pat. Nos. 3,830,862 and 4,022,804. U.S. Pat. No. 4,022,804 is particularly interesting since in one example chloromethyl sulfonic acid bromide is reacted with 2,5-dihydrofuran in the presence of a peroxide and then triethylamine to form 3-chloromethylsulfonyl 2,5-dihydrofuran. While the preparation of this particular sulfone is interesting, the resulting compound is unable to yield an aliphatic conjugated diene upon elimination of the halogen and sulfonyl group.

Often the preparation of such sulfones in the prior art required reaction temperatures in excess of 25° C. or else required exceedingly long reaction times, e.g. in excess of 15 hours. An exception to the elevated temperature or extended reaction time is provided by Example 9 of U.S. Pat. No. 4,022,804 which does, however, in accordance with the teachings of the patent require peroxide catalyst and which results in a sulfone which cannot yield a non-aromatic conjugated diene.

BRIEF DESCRIPTION OF THE INVENTION

In accordance with the present invention, there is provided a novel method for the preparation of sulfones which are structured in a manner which permits the elimination of two hydrogens, two halogen ions and an $SO_2$ group to provide two additional non-aromatic conjugated carbon-carbon double bonds to the compound as a result of such elimination.

The method for the preparation of the sulfones is a one-step method, contrary to prior art complex methods. The reaction temperature is in general well below 25° C. with reaction times usually substantially less than 12 hours. The reactions in general utilize readily available starting materials to prepare novel sulfones and by elimination of halogen, hydrogen and $SO_2$ from the sulfones to prepare certain novel compounds containing carbon-carbon non-aromatic conjugated unsaturated bonds as a result of such elimination.

The novel sulfones in accordance with the present invention are compounds of the formula:

wherein $R_a$ is

wherein $R_b$ is Br and $R_c$ is H except that $R_b$ and $R_c$ together may be an electron pair when $R_6$ is a radical of the formula:

wherein $X_1$ is independently chlorine, bromine or iodine and $R_1$ and $R_2$ are independently at each occurrence hydrogen or, substituted or unsubstituted, phenyl or alkyl where the substituents are halogen or alkoxy or additional —$SO_2Br$ groups; provided that, each carbon atom of $R_1$ or $R_2$ which contains —$SO_2Br$ also contains an $X_1$ group and wherein $R_3$ through $R_9$ are independently —OZ, —$C_6M_5$, —Z, —$SiZ_3$ or —$X_2$, where Z is hydrogen or substituted or unsubstituted phenyl, alkyl, alkenyl or alkynyl; $X_2$ is chlorine, bromine, iodine or fluorine; m is independently at each occurrence Z or $X_2$; $R_3$ and $R_4$ may together be an electron pair; two or more of $R_3$, $R_4$, $R_5$ and $R_6$ may be combined together and with one or more of $C_2$, $C_3$ or $C_4$ to form a ring structure and $R_1$ and $R_2$ may be joined together with $C_1$ to form a ring structure; said method comprising reacting a 1-haloalkyl 1-sulfonyl halide with a second compound of the formula:

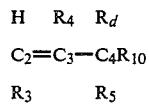

at a temperature below 25° C. for less than 12 hours where $R_3$, $R_4$ and $R_5$ are as previously described, $R_{10}$ is $R_6$ as previously described or $R_{11}$, a radical of the formula:

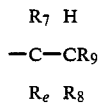

where $R_7$, $R_8$ and $R_9$ are as previously described and $R_d$ is H or when $R_{10}$ is $R_{11}$ forms an electron pair with unshared electron $R_e$; provided that, none of $R_1$ through $R_{11}$ interfere with the reaction of said 1-haloalkyl 1-sulfonyl halide with said second compound; and provided that, elimination of two hydrogens, $X_1$, Br and $SO_2$ from said first compound will yield two additional non-aromatic conjugated carbon-carbon unsaturated bonds as a result of such elimination.

In general, the novel sulfones of the present invention have the formula:

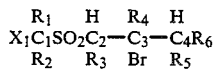

which comprises reacting a second compound of the formula:

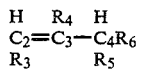

with a 1-haloalkyl 1-sulfonyl halide third compound, where halide is bromine, of the formula:

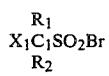

at a temperature below 25° C. for less than 12 hours, wherein $X_1$ is independently chlorine, bromine or iodine and $R_1$ and $R_2$ are independently at each occurrence hydrogen or, substituted or unsubstituted, phenyl or alkyl where the substituents are halogen or alkoxy or additional —$SO_2Br$ groups; provided that, each carbon atom of $R_1$ or $R_2$ which contains —$SO_2Br$ also contains an $X_1$ group. $R_3$ through $R_6$ are independently at each occurrence —OZ, —$SiZ_3$, —$C_6M_5$, —Z or $X_2$ where Z is hydrogen or substituted or unsubstituted phenyl, alkyl, alkenyl or alkynyl; $X_2$ is chlorine, bromine, iodine or fluorine; M is independently at each occurrence Z or $X_2$; $R_3$ and $R_4$ together may comprise an electron pair; two or more of $R_3$, $R_4$, $R_5$ and $R_6$ may be combined together and with one or more of $C_2$, $C_3$ or $C_4$ to form a ring structure; and $R_1$ and $R_2$ may be joined together with $C_1$ to form a ring structure; provided that, none of $R_1$ through $R_6$ interfere with the reaction of the second and third compounds; and provided that, elimination of two hydrogens, $X_1$, Br and $SO_2$ will yield two additional conjugated non-aromatic carbon-carbon double bonds as a result of such elimination.

The novel sulfones of the present invention may also be a compound of the formula:

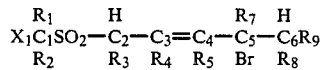

which comprises reacting a second compound of the formula:

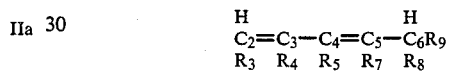

with a 1-haloalkyl 1-sulfonyl halide third compound, as previously described, at a temperature below 25° C. for less than 12 hours. $R_3$ through $R_5$ and $R_7$ through $R_9$ are independently at each occurrence —OZ,—$SiR_3$,—$C_6M_5$,—Z or —$X_2$, where Z is hydrogen or, substituted or unsubstituted, phenyl, alkyl, alkenyl, or alkynyl. $X_2$ is fluorine, chlorine, bromine or iodine. M is independently at each occurrence Z or $X_2$. $R_3$ and $R_4$ together may comprise an electron pair. Two or more of $R_3$, $R_4$, $R_5$, $R_7$, $R_8$ and $R_9$ may be joined together with one or more of $C_2$, $C_3$, $C_4$, $C_5$ or $C_6$ to form a ring structure. $R_1$ and $R_2$ may be joined together with $C_1$ to form a ring structure. None of $R_1$ through $R_5$ or $R_7$ through $R_9$ may be groups which interfere with the reaction of the second and third compounds. As previously discussed with respect to all starting compositions and compounds of the present invention, none of the $R_1$ through $R_9$ groups may interefere with the reaction of the initial unsaturated compound and the 1-haloalkyl 1-sulfonyl halide.

Such undesirable groups are usually groups which are bases, radical scavangers, strong nucleophiles, large groups which substantially sterically hinder the reactivity of unsaturated bond which is to react with the sulfonyl halide and highly electron withdrawing groups which substantially reduce the reactivity of such unsaturated bond. Examples of unsuitable bases are amino groups such as dimethylamino or diethylamino. Examples of unsuitable radical scavengers are thiol groups, hydroxyphenyl groups, and thiocarbonyl groups. Examples of unsuitable nucleophiles are —OM or —SM or where M is an alkali metal. Examples of sterically hindering groups are tertiary alkyl groups directly on a carbon atom of the double bond which is to react with the 1-haloalkyl 1-sulfonyl halide. Examples of electron withdrawing groups are sulfonyl groups directly on a carbon atom of the double bond which is to react with the 1-haloalkyl 1-sulfonyl halide.

Elimination of two hydrogens, $X_1$, Br and $SO_2$ must yield two additional conjugated non-aromatic carbon-carbon double bonds as a result of such elimination.

The invention further comprises a method for preparation of an aliphatically unsaturated compound by reacting the novel sulfones of the present invention with sufficient base to eliminate $X_2$ and an atom of hydrogen from $C_2$ and the method for preparing compounds having conjugated unsaturation reacting the novel sulfones with sufficient base to eliminate $X_1$, bromine, two atoms of hydrogen and $SO_2$.

In general, such a method is a method for increasing the chain length of a starting compound containing carbon-carbon aliphatic unsaturation while simultaneously adding additional aliphatic unsaturation to the starting compound in the form of olefinic unsaturation. The method comprises reacting the starting compound with a 1-haloalkyl 1-sulfonyl halide at a temperature below 25° C. for less than 12 hours followed by treating the reaction product with base in one or two steps to eliminate the halogens and $SO_2$ from the reaction product which was provided by the 1-haloalkyl 1-sulfonyl halide and to eliminate two hydrogens. If two steps are used, a single halogen, Br on $C_3$ in formula III and a hydrogen on $C_2$ are eliminated in the first step and $X_1$, $SO_2$ and the hydrogen on $C_4$ in formula III and $C_6$ in formula V are eliminated in the second step.

The invention also includes novel unsaturated sulfones formed by the elimination of bromine and the hydrogen atom on the $C_2$ carbon atom of preceding formulas III and V which unsaturated sulfones may be represented by the generic formula:

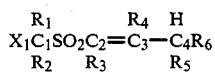

and

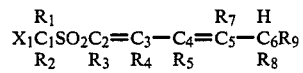

where $R_1$ through $R_9$ and $X_1$ are as previously described.

The invention further includes particular novel aliphatic compounds of the formula:

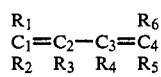

DETAILED DESCRIPTION OF THE INVENTION

As previously discussed, the present invention includes the preparation of certain desirable sulfones by reacting a 1-haloalkyl 1-sulfonyl halide with a compound containing carbon-carbon aliphatic unsaturation which compound, containing the aliphatic unsaturation, typically has the generic formula:

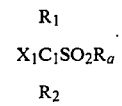

In general, 1-haloalkyl 1-sulfonyl halides have been known. For example, $BrCH_2SO_2Cl$ and $BrCH_2SO_2Br$ are described in U.S. Pat. No. 3,850,972 and $ClCH_2SO_2Br$ as described in U.S. Pat. No. 4,022,804.

The 1-haloalkyl 1-sulfonyl halide used in the present invention is 1-haloalkyl 1-sulfonyl bromide which in general has the formula:

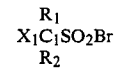

wherein $X_1$ is independently chlorine, bromine or iodine and $R_1$ and $R_2$ are independently at each occurrence hydrogen or, substituted or unsubstituted, phenyl or alkyl where the substituents are halogen or $-OR$ where R is alkyl. Either $R_1$ or $R_2$ may also contain additional $-SO_2Br$ groups provided that each carbon atom of $R_1$ or $R_2$ which contains an $-SO_2Br$ group also contains an $X_1$ group.

Such disulfonyl compounds can react with compounds containing carbon-carbon unsaturation to link such compounds and can react with compounds containing polyunsaturation to create polymeric sulfones which can in turn be treated with a base to eliminate halogen, hydrogen and $SO_2$ to yield polymeric products containing polyunsaturation. Another formula for representing the 1-haloalkyl 1-sulfonyl bromide is $X_1RSO_2Br$ where R is a methylene group connecting $X_1$ and $SO_2Br$ which methylene group may be substituted with additional substituted or unsubstituted alkyl groups or substituted or unsubstituted phenyl groups as previously described.

Examples of suitable 1-haloalkyl 1-sulfonyl halides are as follows:

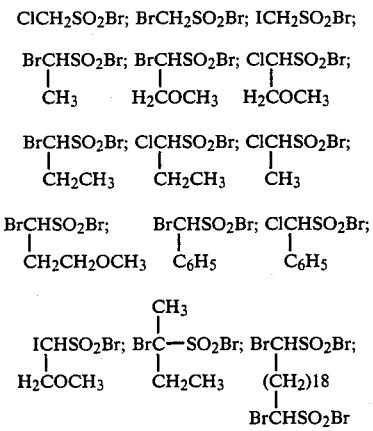

As previously discussed, the compound with which the 1-haloalkyl 1-sulfonyl bromide is reacted is an aliphatically unsaturated compound meaning that the compound contains at least one ethylenically or acetylenically unsaturated bond.

In order to meet the requirements of the present invention, the unsaturated compound must have the generic formula IV as previously described. In this formula, the $C_4$ carbon atom must either contain a hydrogen atom or must be double bonded to an adjacent $C_5$ carbon atom which in turn must be bonded to a $C_6$ carbon atom which contains hydrogen. It is this particular organization of the compound with which the 1-haloalkyl 1-sulfonyl halide is reacted which permits the formation of conjugated aliphatic unsaturation when the resulting sulfone is treated to eliminate two hydrogens, $X_1$, Br and $SO_2$. Formulas VII and X are exemplary of such starting unsaturated compounds.

In reacting the 1-haloalkyl 1-sulfonyl halide with the initial unsaturated compound, the unsaturated compound and the haloalkyl sulfonyl halide are usually mixed together in approximately an equal molar ratio. In certain circumstances, however, it may be desirable to use an excess of one of the components. For example, it has been found that an excess of the 1-haloalkyl sulfonyl bromide is desirable when the unsaturated compound is acetylenically unsaturated.

The rate of reaction may be controlled by gradual addition of one of the reactants to the other.

No catalyst in the form of a peroxide or metal salt is necessary and is usually undesirable due to potential contamination resulting from such catalysts. The reaction temperature is below 25° C., usually below 20° C. and most preferably below 5° C. to avoid side reactions which contaminate the product as occurs in prior art. Desirably, the reaction is initiated by light which may be in the ultraviolet or visible range. The reaction to form the sulfone is believed to be a free radical reaction. Subsequent elimination reactions to form unsaturates are believed to involve elimination of hydrogen and halide ions. When reference is made to elimination of hydrogen or halide, it is understood that ions are being eliminated.

The reaction to form the sulfone may be carried out in the presence or absence of solvents. Examples of suitable solvents are aliphatic and cycloaliphatic ethers, e.g. diethyl ether, tetrahydrofuran, dioxane and 1,2-diethoxyethane, aliphatic and cycloaliphatic hydrocarbons such as petroleum ether, gasoline, cyclohexane, aromatic hydrocarbons such as benzene, toluene and chlorobenzene; halogenated aliphatic hydrocarbons such as methylene chloride, chloroform and carbon tetrachloride; carbon disulfide, esters, especially ethyl acetate; ketones, especially acetone and diethyl ketone; acetonitrile; nitromethane; lower alcohols such as ethanol or isopropanol; or water. One of the reactants, preferably the unsaturated initial compound, used in excess may also serve as the solvent. Methylene chloride is the preferred solvent.

In accordance with the present invention, the yield of sulfone from the reaction is in excess of 50 percent and preferably in excess of 95 percent.

Examples of starting aliphatically unsaturated compounds for reaction with 1-haloalkyl 1-sulfonyl halides are shown in Table A.

TABLE A

| | | |
|---|---|---|
| (1) | 2-butene | |
| (2) | 1-pentene | |
| (3) | 1-octene | |
| (4) | isobutene | |
| (5) | 3-hexene | |
| (6) | 1-decene | |
| (7) | 1-dodecene | |
| (8) | 1-hexadecene | |
| (9) | 1-octadecene | |
| (10) | 3-ethoxy-2-methyl-1-propene | |
| (11) | 1,4-dimethoxy-2-butene | |

TABLE A-continued

| | |
|---|---|
| (12) | 1,9-decadiene |
| (13) | 1,4-octadiene |
| (14) | piperylene |
| (15) | allyl cyanide |
| (16) | methylenecyclohexane |
| (17) | vinylcyclohexane |
| (18) | allylcyclohexane |
| (19) | ethylidenecyclopentane |
| (20) | allylbenzene |
| (21) | methallylbenzene |
| (22) | 1-phenyl-2-butene |
| (23) | cyclopentene |
| (24) | cyclohexene |
| (25) | cyclododecene |
| (26) | cycloheptene |
| (27) | 1,3-cyclooctadiene |
| (28) | 1-hexyne |
| (29) | 1-octyne |
| (30) | propargylonitrile |
| (31) | 1,4-dimethoxy-2-butyne |
| (32) | 1,3-nonadiene |
| (33) | 1-methylcyclohexene |
| (34) | methylenecycloheptane |
| (35) | 7-tetradecene |
| (36) | 3-hexyne |
| (37) | 1-methylcycloheptene |
| (38) | 3-phenoxypropylene |
| (39) | 11-hydroxy-1-undecene |
| (40) | allyl trimethylsilane |
| (41) | 1,5-cyclooctadiene |
| (42) | 1,7-octadiene |
| (43) | 1,5-hexadiene |
| (44) | 1,11-dodecadiene |
| (45) | 1-heptene |
| (46) | 5-decene |
| (47) | 2-octene |
| (48) | methylene cyclooctane |
| (49) | cyclooctene |
| (50) | 1,3-heptadiene |

Examples of sulfones which may be prepared in accordance with the method of the present invention from the compounds in Table A and numbered correspondingly are as shown in Table B.

TABLE B

| | |
|---|---|
| (1) | 2-bromomethanesulfonyl-3-bromobutane |
| (2) | 1-bromomethanesulfonyl-2-bromopentane |
| (3) | 1-bromomethanesulfonyl-2-bromooctane |
| (4) | 1-bromomethanesulfonyl-2-bromo-2-methylpropane |
| (5) | 3-bromomethanesulfonyl-4-bromohexane |
| (6) | 1-bromomethanesulfonyl-2-bromodecane |
| (7) | 1-bromomethanesulfonyl-2-bromododecane |
| (8) | 1-bromomethanesulfonyl-2-bromohexadecane |
| (9) | 1-bromomethanesulfonyl-2-bromooctadecane |
| (10) | 1-bromomethanesulfonyl-2-bromo-3-ethoxy-2-methylpropane |
| (11) | 1-bromomethanesulfonyl-3-bromo-1,4-dimethoxybutane |
| (12a) | 1,10-bis(bromomethanesulfonyl)-2,9-dibromodecane |
| (12b) | 1-bromomethanesulfonyl-2-bromo-9-decene |
| (13a) | 1-bromomethanesulfonyl-2-bromo-4-octene |
| (13b) | 1,4-bis(bromomethanesulfonyl)-2,5-dibromooctane |
| (13c) | 1,5-bis(bromomethanesulfonyl)-2,4-dibromooctane |
| (14) | 1-bromomethanesulfonyl-4-bromo-2-pentene |
| (15) | 3-bromomethanesulfonyl-2-bromopropionitrile |
| (16) | (1-bromocyclohexyl)methyl bromomethyl sulfone |
| (17) | 1-bromomethanesulfonyl-2-bromo-2-cyclohexylethane |
| (18) | 1-bromomethanesulfonyl-2-bromo-3-cyclohexylpropane |
| (19) | (1-bromocyclopenyl)ethyl bromomethyl sulfone |
| (20) | 1-bromomethanesulfonyl-2-bromo-3-phenylpropane |
| (21) | 1-bromomethanesulfonyl-2-bromo-2-methyl-3-phenylpropane |
| (22) | 2-bromomethanesulfonyl-2-bromo-1-phenylbutane |
| (23) | 2-bromocyclopentyl bromomethyl sulfone |
| (24) | 2-bromocyclohexyl bromomethyl sulfone |
| (25) | 2-bromocyclododecyl bromomethyl sulfone |
| (26) | 2-bromocycloheyxl bromomethyl sulfone |
| (27) | 1-bromomethanesulfonyl-4-bromo-2-cyclooctene |
| (28) | 1-bromomethanesulfonyl-2-bromo-1-hexene |
| (29) | 1-bromomethanesulfonyl-2-bromo-1-octene |
| (30) | 1-bromomethanesulfonyl-2-bromo-3-cyano-1-propene |
| (31) | 2-bromomethanesulfonyl-3-bromo-1,4-dimethoxy-2-butene |

TABLE B-continued

- (32) 1-bromomethanesulfonyl-4-bromo-2-nonene
- (33) 2-bromo-2-methylcyclohexyl bromomethyl sulfone
- (34) (1-bromocycloheptyl)methyl bromomethyl sulfone
- (35) 2-bromomethanesulfonyl-8-bromotetradecane
- (36) 3-bromomethanesulfonyl-4-bromo-3-hexene
- (37) 2-bromo-2-methylcycloheptyl bromomethyl sulfone
- (38) 1-bromomethanesulfonyl-2-bromo-3-phenoxypropane
- (39) 1-bromomethanesulfonyl-2-bromo-11-hydroxyundecane
- (40) 1-bromomethanesulfonyl-2-bromo-3-trimethylsilylpropane
- (41) 1-bromomethanesulfonyl-2-bromo-cycloöct-5-ene
- (42a) 1-bromomethanesulfonyl-2-bromo-7-octene
- (42b) 1,7-bis(bromomethanesulfonyl)-2,8-dibromooctane
- (43) 1-bromomethanesulfonyl-2-bromo-5-hexene
- (44) 1-bromomethanesulfonyl-2-bromo-11-dodecene
- (45) 1,11-bis(bromomethanesulfonyl)-2,12-dibromododecane
- (46) 1-bromomethanesulfonyl-2-bromoheptane
- (46) 5-bromomethanesulfonyl-6-bromodecane
- (47) 2-bromomethanesulfonyl-3-bromooctane
- (48) (1-bromocyclooctyl)methyl bromomethyl sulfone
- (49) 2-bromocyclooctyl bromomethyl sulfone
- (50) 1-bromomethanesulfonyl-4-bromo-2-heptene The sulfones prepared in accordance with the present invention may be treated with a base to eliminate either Br and H or Br, H, $X_1$, H and $SO_2$ to obtain new unsaturated compounds.

Suitable bases are bases which are not nucleophilic since such bases yield undesirable reaction products. When only Br (not $X_1$) and H are being eliminated a weak base such as a trialkylamine may be used. The alkyl groups should be $C_2$ or higher to prevent nucleophilic attack. When the $X_1$ halogen, hydrogen and $SO_2$ are being eliminated, a stronger base such as t-butyl-OM where M is Li, Na, K or Cs or t-amyl-OM or in general:

where R is alkyl or aryl.

In general, such bases are sterically hindered by groups at at least three positions on the base carbon atom to prevent them from acting as nucleophiles.

Usually a solvent is used during the elimination reaction with base. Such solvents are usually tertiary alcohols such as t-butyl or t-amyl alcohol. Cosolvents such as cyclic or acyclic ethers may be used.

A list of sulfones wherein Br and a hydrogen have been eliminated from correspondingly numbered compounds of Table B to form new unsaturated sulfone compounds are as shown in Table C.

TABLE C

- (1) 2-bromomethanesulfonyl-2-butene
- (2) 1-bromomethanesulfonyl-1-pentene
- (3) 1-bromomethanesulfonyl-1-octene
- (4) 1-bromomethanesulfonyl-2-methyl-1-propene
- (5) 3-bromomethanesulfonyl-3-hexene
- (6) 1-bromomethanesulfonyl-1-decene
- (7) 1-bromomethanesulfonyl-1-dodecene
- (8) 1-bromomethanesulfonyl-1-hexadecene
- (9) 1-bromomethanesulfonyl-1-octadecene
- (10) 1-bromomethanesulfonyl-3-ethoxy-2-methyl-2-propene
- (11) 2-bromomethanesulfonyl-1,4-dimethoxy-2-butene
- (12a) 1,10-bis(bromomethanesulfonyl)-1,9-decadiene
- (12b) 1-bromomethanesulfonyl-1,9-decadiene
- (13a) 1-bromomethanesulfonyl-1,4-octadiene
- (13b) 1,4-bis(bromomethanesulfonyl)-1,4-octadiene
- (13c) 1,5-bis(bromomethanesulfonyl)-1,4-octadiene
- (14) 1-bromomethanesulfonyl-1,3-pentadiene
- (15) 3-bromomethanesulfonyl-2-acrylonitrile
- (16) alpha-bromomethanesulfonyl methylenecyclohexane
- (17) 1-bromomethanesulfonyl-2-cyclohexylethene TABLE C-continued

- (18) 1-bromomethanesulfonyl-3-cyclohexyl-1-propene
- (19) alpha-bromomethanesulfonyl-ethylidenecyclopentane
- (20) 1-bromomethanesulfonyl-3-phenyl-1-propene
- (21) 1-bromomethanesulfonyl-2-methyl-3-phenyl-1-propene
- (22) 2-bromomethanesulfonyl-1-phenyl-2-butene
- (23) 1-cyclopentenyl (or 3-cyclopentenyl) bromomethyl sulfone
- (24) 1-cyclohexenyl (or 3-cyclohexenyl) bromomethyl sulfone
- (25) 1-cyclododecenyl (or 3-cyclododecenyl) bromomethyl sulfone
- (26) 1-cycloheptenyl (or 3-cycloheptenyl) bromomethyl sulfone
- (27) 1-bromomethanesulfonyl-1,3-cyclooctadiene
- (28) 1-bromomethanesulfonyl-1-hexyne (or 1-bromomethanesulfonyl-2-bromo-1,3-hexadiene)
- (29) 1-bromomethanesulfonyl-1-octyne (or 1-bromomethanesulfonyl-2-bromo-1,3-octadiene)
- (30) 1-bromomethanesulfonylpropargylonitrile
- (31) 2-bromomethanesulfonyl-3-bromo-1,4-dimethoxy-2-butene
- (32) 1-bromomethanesulfonyl-1,3-nonadiene
- (33) 2-methyl-1-cyclohexenyl bromomethyl sulfone
- (34) alpha-bromomethanesulfonyl methylenecycloheptane
- (35) 7-bromomethanesulfonyl-7-tetradecene
- (36) 3-bromomethanesulfonyl-3-hexene
- (37) 2-methyl-1-cycloheptenyl bromomethyl sulfone
- (38) 1-bromomethanesulfonyl-3-phenoxy-1-propene
- (39) 1-bromomethanesulfonyl-11-hydroxy-1-undecene
- (40) 1-bromomethanesulfonyl-3-trimethylsilyl-1-propene
- (41) 1-bromomethanesulfonyl-1,5-cyclooctadiene
- (42a) 1-bromomethanesulfonyl-1,7-octadiene
- (42b) 1,7-bis(bromomethanesulfonyl)-1,7-octadiene
- (43) 1-bromomethanesulfonyl-1,5-hexadiene
- (44a) 1-bromomethanesulfonyl-1,11-dodecadiene
- (44b) 1,11-bis(bromomethanesulfonyl)-1,11-dodecadiene
- (45) 1-bromomethanesulfonyl-1-heptene
- (46) 5-bromomethanesulfonyl-5-decene
- (47) 2-bromomethanesulfonyl-2-octene
- (48) alpha-bromomethanesulfonyl methylenecyclooctane
- (49) 1-cyclooctenyl (or 3-cyclooctenyl) bromomethyl sulfone
- (50) 1-bromomethanesulfonyl-1,3-heptadiene A list of aliphatically polyunsaturated compounds of the present invention which may be made by elimination of two halogens, two hydrogens and $SO_2$ from correspondingly numbered sulfones of Table B or by elimination of one halogen, a hydrogen and $SO_2$ from the correspondingly numbered compounds of Table C are set forth in Table D as follows:

TABLE D

- (1) Isoprene
- (2) 1,3-hexadiene
- (3) 1,3-nonadiene
- (4) Isoprene
- (5) 2-ethyl-1,3-pentadiene
- (6) 1,3-undecadiene
- (7) 1,3-tridecadiene
- (8) 1,3-heptadecadiene
- (9) 1,3-nonadecadiene
- (10) 1-ethoxy-2-methyl-1,3-butadiene
- (11) 3-methoxymethyl-1-methoxy-1,3-butadiene
- (12a) 1,3,9,11-dodecatetraene
- (12b) 1,3,10-undecatriene
- (13a) 1,3,5-nonatriene
- (13b) 2-butyl-1,3,5-hexatriene
- (13c) 6-propyl 1,3,6-heptatriene
- (14) 1,3,5-hexatriene
- (15) 1-cyano-1,3-butadiene
- (16) 1-vinyl-1-cyclohexene
- (17) 2-propenylidene cyclohexane
- (18) 1-cyclohexyl-1,3-butadiene
- (19) 1-(1-methylvinyl)-cyclopentene
- (20) 1-phenyl-1,3-butadiene
- (21) 2-methyl-1-phenyl-1,3-butadiene
- (22) 3-methyl-1-phenyl-1,3-butadiene
- (23) 3-methylene-1-cyclopentene
- (24) 3-methylene-1-cyclohexene
- (25) 3-methylene-1-cyclododecene

TABLE D-continued

| | |
|---|---|
| (26) | 3-methylene-1-cycloheptene |
| (27) | 5-methylene-1,3-cyclooctadiene |
| (28) | hept-1-ene-3-yne |
| (29) | non-1-ene-3-yne |
| (30) | 1-cyanobut-1-ene-3-yne |
| (31) | 1-methoxy-3-methoxymethylbut-3-ene-1-yne |
| (32) | 1,3,5-decatriene |
| (33) | 1,2-bismethylenecyclohexane |
| (34) | 1-vinyl-1-cycloheptene |
| (35) | 2-hexyl-1,3-nonadiene |
| (36) | 2-ethyl-1,3-pentadiene |
| (37) | 1,2-bismethylenecycloheptane |
| (38) | 1-phenoxy-1,3-butadiene |
| (39) | 11-hydroxy-1,3-undecadiene |
| (40) | 1-trimethylsilyl-1,3-butadiene |
| (41) | 1-methylene-3,5-cyclooctadiene |
| (42a) | 1,3,8-nonatriene |
| (42b) | 1,3,7,9-decatetraene |
| (43) | 1,3,6-heptatriene |
| (44a) | 1,3,12-tridecatriene |
| (44b) | 1,3,11,13-tetradecatetraene |
| (45) | 1,3-octadiene |
| (46) | 2-butyl-1,3-heptadiene |
| (47) | 2-methyl-1,3-octadiene |
| (48) | 1-vinyl-1-cyclooctene |
| (49) | 3-methylene-1-cyclooctene |
| (50) | 1,3,5-octatriene |

Alkyl, alkenyl and alkynyl as used herein, unless specified otherwise, means a carbon chain of any length but is commonly less than 30 carbon atoms and usually less than 20 carbon atoms.

The following specific examples serve to illustrate and not limit the present invention. Unless otherwise indicated, all parts and percentages are by weight. Yields are stepwise yields.

EXAMPLE 1

(1,2-bismethylene cyclohexane)

A mixture of 1-methycyclohexene (0.4 g) and bromomethanesulfonyl bromide (1.3 g) in methylene chloride (4 mL) was irradiated at −15° C. with an ultraviolet lamp for 2 hours. The reaction mixture was diluted with methylene chloride, a small amount of solid potassium carbonate was added and the solution was filtered. The reaction mixture was diluted with methylene chloride (50 mL) and washed with 20% sodium bisulfite solution and water. The aqueous layer was separated, dried over anhydrous magnesium sulfate and the methylene chloride removed in vacuo to give solid 2-bromo-2-methylcyclohexyl bromomethyl sulfone (1.27 g, 91% yield) which was characterized by IR and NMR spectroscopy.

The latter compound (1.2 g) was dissolved in 10 mL of 1:9 THF (tetrahydrofuran):tert-butanol and added dropwise to an ice cold solution of potassium tert-butoxide (1.31 g) in 25 mL of 1:9 THF:tert-butanol. The reaction mixture was stirred in ice for 0.5 hours and at room temperature for 0.25 hours. The reaction mixture was diluted with water (25 mL) and extracted with 2-methylbutane (2×25 mL). The combined organic layer was washed with water (7×50 mL). The organic layer was separated, dried with anhydrous magnesium sulfate, filtered and the solvent removed at atmospheric pressure using a Vigreaux column to give a liquid. Distillation gave 0.24 g (62% yield) of 1,2-bis(methylene)-cyclohexane as established by proton and carbon-13 NMR and IR analysis.

EXAMPLE 2

(3-methylene cyclooctene)

A mixture of cyclooctene (2.2 g) and bromomethanesulfonyl bromide (4.8 g) in methylene chloride (6 mL) was irradiated at −20° C. with an ultraviolet lamp for 1 hour. The reaction mixture was diluted with methylene chloride (10 mL), treated with a small quantity of potassium carbonate, filtered and concentrated in vacuo giving 2-bromocyclooctyl bromomethyl sulfone as an oil (5.9 g, 85% yield) which was characterized by IR and NMR spectroscopy.

The latter compound (5.2 g) was dissolved in 30 mL of 1:9 THF:tert-butanol and added dropwise to an ice cold solution of potassium tert-butoxide (5.9 g) in 100 mL of 1:9 THF:tert-butanol. The reaction mixture was stirred in ice for 0.5 hours and at room temperature for 0.5 hour. The reaction mixture was diluted with water (200 mL) and extracted with pentane (2×50 mL). The combined organic layer was washed with water (6×100 mL). The organic layer was separated, dried with anhydrous magnesium sulfate, filtered and the solvent removed in vacuo to give an oil. Distillation gave 1.03 g (57% yield, of 3-methylenecyclooctene as established by proton and carbon-13 NMR, IR and mass spectroscopic analysis.

EXAMPLE 3

(1-vinyl cycloheptene)

A mixture of methylenecycloheptane (3.3 g) and bromomethanesulfonyl bromide (7.14 g) in methylene chloride (10 mL) was irradiated at −20° C. with an ultraviolet lamp for 1 hour. Evaporation of the solvent gave a solid which was washed with pentane. This solid (9.7 g) was dissolved in methylene chloride (150 mL), chilled in ice and treated dropwise with a solution of triethylamine (3.3 g) in methylene chloride (20 mL). The reaction mixture was stirred for 0.5 hours, washed with dilute HCl and water. The organic layer was separated, dried over anhydrous magnesium sulfate and the methylene chloride removed in vacuo to give oily bromomethanesulfonylmethylene cycloheptane (7.0 g, 96% yield) which was characterized by IR and NMR spectroscopy.

The latter compound (6.7 g) was dissolved in 40 mL of 1:9 THF:tert-butanol and added dropwise to an ice cold solution of potassium tert-butoxide (8.44 g) in 100 mL of 1:9 THF:tert-butanol. The reaction mixture was stirred in ice for 0.5 hours and at room temperature for 0.5 hours. The reaction mixture was diluted with water (200 mL) and extracted with pentane (2×50 mL). The combined organic layer was washed with water (7×150 mL). organic layer was separated, dried with anhydrous magnesium sulfate, filtered and the solvent removed at atmospheric pressure using a Vigreaux column to give a liquid. Distillation gave 2.6 g (85% yield) of 1-vinyl cycloheptene as established by NMR and IR analyis.

EXAMPLE 4

(2-n-hexyl-1,3-nonadiene)

A mixture of 7-tetradecene (3.92 g) and bromomethanesulfonyl bromide (7.14 g) in methylene chloride (8 mL) was irradiated at −15° C. with an ultraviolet lamp for 2 hours. A small amount of solid potassium carbonate was added and then removed by filtration. The reaction mixture was diluted with methylene chloride (100 mL) and triethylamine (3.0 g) was added. The reaction mixture was heated on a steam bath for 1 hour. The reaction mixture was washed with dilute HCl and water. The methylene chloride layer was separated, dried over anhydrous magnesium sulfate and the methylene chloride removed in vacuo to give 7.1 g (100% yield) of oily 7-tetradecenyl bromomethyl sulfone which was characterized by IR and NMR spectroscopy.

The latter compound (7.0 g) was dissolved in 30 mL of 1:9 THF:tert-butanol and added dropwise to an ice cold solution of potassium tert-butoxide (0.7 g) in 100 mL of 1:9 THF:tert-butanol. The reaction mixture was stirred in ice for 0.5 hours and at room temperature for 0.5 hours. The reaction mixture was diluted with water (200 mL) and extracted with hexane (2×50 mL). The combined organic layer was washed with water (7×150 mL). The organic layer was separated, dried with anhydrous magnesium sulfate, filtered and the solvent removed in vacuo to give an oil. Distillation gave 2.9 g (71% yield; bp$_{0.034\ mm}$ 60°–62° C.) of 2-n-hexyl-1,3-nonadiene as established by proton and carbon-13 NMR and IR analysis.

EXAMPLE 5

(1,3-nonadiene)

A mixture of 1-octene (2.82 g) and bromomethanesulfonyl bromide (6.0 g) in methylene chloride (4 mL) was irradiated at −20° C. with an ultraviolet lamp for 0.5 hours. A small amount of solid potassium carbonate was added and then removed by filtration. The reaction mixture was diluted with methylene chloride (50 mL), cooled in ice and treated with a solution of triethylamine (4.45 g) in 10 mL of methylene chloride. The reaction mixture was stirred for 0.25 hours and was washed with dilute HCl and water. The methylene chloride layer was separated, dried over anhydrous magnesium sulfate and the methylene chloride removed in vacuo to give 5.9 g (97% yield) of oily 1-octenyl bromomethyl sulfone which was characterized by IR and NMR spectroscopy.

The latter compound (5.4 g) was dissolved in 20 mL of 1:9 THF:tert-butanol and added dropwise to an ice cold solution of potassium tert-butoxide (6.75 g) in 100 mL of 1:9 THF:tert-butanol. The reaction mixture was stirred in ice for 1 hour and at room temperature for 0.5 hours. The reaction mixture was diluted with water (200 mL) and extracted with pentane (2×75 mL). The combined organic layer was washed with water (4×150 mL). The organic layer was separated, dried with anhydrous magnesium sulfate, filtered and the solvent removed in vacuo to give an oil. Distillation gave 1.79 g (72% yield) of a 2:1 mixture of (Z)- and (E)-1,3-nonadiene as established by NMR, IR and capillary GC analysis.

EXAMPLE 6

(1,3,9,11-dodecatetraene)

A mixture of 1,9-decadiene (1.38 g) and bromomethanesulfonyl bromide (4.8 g) in methylene chloride (3 mL) was irradiated at −20° C. with an ultraviolet lamp for 0.75 hours. A small amount of solid potassium carbonate was added and then removed by filtration and the solvent was removed in vacuo to give 6.3 g of a solid, identified by NMR and IR as 2,9-dibromo-1,10-bis(bromomethanesulfonyl)-decane. A solution of 4.4 g of this solid was dissolved in 40 mL of methylene chloride, the mixture was cooled in ice and treated with a solution of triethylamine (1.83 g) in 15 mL of methylene chloride. The reaction mixture was stirred for 0.25 hours and was washed with dilute HCl and water. The methylene chloride layer was separated, dried over anhydrous magnesium sulfate and the methylene chloride removed in vacuo to give 2.6 g (81% yield) of solid 1,10-bis-(bromomethanesulfonyl)-1,9-decadiene which was characterized by IR and NMR spectroscopy.

The latter compound (2.0 g) was dissolved in 50 mL of 1:4 THF:tert-butanol and added dropwise to an ice cold solution of potassium tert-butoxide (3.00 g) in 100 mL of 1:4 THF:tert-butanol. The reaction mixture was stirred in ice for 0.5 hours and at room temperature for 2 hours. The reaction mixture was diluted with water and extracted with pentane. The combined organic layer was washed with water. The organic layer was separated, dried with anhydrous magnesium sulfate, filtered and the solvent removed in vacuo to give an oil. Distillation gave 0.34 g (48% yield) of 1,3,9,11-dodecatetraene as established by proton and carbon-13 NMR and IR analysis.

EXAMPLE 7

(2-ethyl-hex-1-ene-3-yne)

A mixture of 3-hexyne (1.6 g) and bromomethanesulfonyl bromide (2.38 g) in methylene chloride (3 mL) was irradiated at −20° C. with an ultraviolet lamp for 2 hours. A small amount of solid potassium carbonate was added and then removed by filtration. The solution was concentrated in vacuo to give 3-bromo-4-(bromomethanesulfonyl)-hex-3-ene (2.73 g, 85% yield) as a white solid (mp 96°–97° C., after recrystallization from ethanol) which was characterized by IR and NMR spectroscopy.

The latter compound (3.2 g) was dissolved in 15 mL of 1:2 THF:tert-butanol and added dropwise to an ice cold solution of potassium tert-butoxide (4.5 g) in 66 mL of 1:10 THF:tert-butanol. The reaction mixture was stirred in ice for 0.5 hours and at room temperature for 1 hour. The reaction mixture was diluted with water and extracted with pentane. The combined organic layer was washed with water. The organic layer was separated, dried with anhydrous magnesium sulfate, filtered and the solvent removed by distillation to give an oil. Distillation gave 0.43 g (46% yield) of 2-ethyl-hex-1-ene-3-yne as established by proton and carbon-13 NMR and IR analysis.

EXAMPLE 8

(1,3,5-undecatriene)

A mixture of 1,3-decadiene (2.8 g) and bromomethanesulfonyl bromide (4.76 g) in methylene chloride (3 mL) was irradiated at −20° C. with an ultraviolet lamp for 1 hour. The solution was filtered through potassium carbonate and concentrated in vacuo giving 4-bromo-1-(bromomethanesulfonyl)-dec-2-ene (7.5 g, 100%), characterized by NMR and IR spectroscopy. This material was then dissolved in 30 mL of methylene chloride, the solution was chilled in ice and treated dropwise with a solution of triethylamine (3.0 g) in methylene chloride (10 mL). The reaction mixture was stirred for 0.5 hours, washed with cold 10% HCl and water. The organic layer was separated, dried over anhydrous magnesium sulfate and the methylene chloride removed in vacuo to give a solid, 1-(bromomethanesulfonyl)-1,3-decadiene (5.4 g, 92% yield) which was characterized by IR and NMR spectroscopy.

The latter compound (4.4 g) was dissolved in 143 mL of 1:2 THF:tert-butanol and added simultaneously with a solution of potassium tert-butoxide (4.2 g) in 143 mL of 1:2 THF:tert-butanol at room temperature to 715 mL of tert-butanol over a period of 24 hours under argon. The reaction mixture was diluted with water and extracted with pentane. The combined organic layer was washed with water. The organic layer was separated, dried with anhydrous magnesium sulfate, filtered and the solvent removed in vacuo giving a yellow liquid. Vacuum distillation gave 0.55 g (24% yield) of 1,3,5-undecatriene as established by NMR, UV and IR analysis.

EXAMPLE 9

(2,4-octadiene)

A mixture of 1-hexene (10.0 g) and 1-bromoethanesulfonyl bromide (3.0 g) in methylene chloride (5 mL) was irradiated at $-20°$ C. with an ultraviolet lamp for 1 hour. Concentration of the solution in vacuo gave 3.55 g (91% yield) of an oil identified by NMR and IR spectroscopy as 2-bromohexyl 1'-bromoethyl sulfone. This latter compound was dissolved in 6 mL of methylene chloride, chilled in ice and treated dropwise with a solution of triethylamine (1.7 g) in 2 mL of methylene chloride. The reaction mixture was stirred for 0.5 hours and washed with dilute HCl (5%) and water. The organic layer was separated, dried over anhydrous magnesium sulfate and the methylene chloride removed in vacuo to give oily 1-hexenyl 1'-bromoethyl sulfone (1.77 g, 70% yield) which was characterized by IR and NMR spectroscopy.

The latter compound was dissolved in 2 mL of 1:10 THF:tert-butanol and added dropwise to an ice cold solution of potassium tert-butoxide (2 g) in 20 mL of 1:10 THF:tert-butanol. The reaction mixture was stirred in ice for 0.5 hours and at room temperature for 1 hour. The reaction mixture was diluted with water (50 mL) and extracted with hexane (2×20 mL). The combined organic layer was washed with saturated sodium chloride solution (6×10 mL). The organic layer was separated, dried with anhydrous magnesium sulfate, filtered and the solvent removed in vacuo to give a liquid. Distillation gave 0.26 g (36% yield) of 2,4-octadiene as established by NMR and IR analysis.

What is claimed is:

1. A method for the preparation of conjugated aliphatically unsaturated compounds, which comprises the steps of reacting a starting compound containing carbon-carbon aliphatic unsaturation with a 1-haloalkyl 1-sulfonyl bromide at a temperature below 25° for less than 12 hours followed by treating the reaction product with sufficient base to eliminate two hydrogen ions, one halogen ion, one bromine ion and an $SO_2$ group from the reaction product to yield a compound having two conjugated carbon-carbon double bonds.

2. The method of claim 1 wherein the 1-haloalkyl 1-sulfonyl bromide has the generic formula $X_1RSO_2Br$ where $X_1$ is Cl, Br or I and R is an alkylene group of up to 20 carbon atoms and the reaction temperature of the starting compound with the 1-haloalkyl 1-sulfonyl bromide is maintained below 20° C.

3. The method of claim 2 wherein the 1-haloalkyl 1-sulfonyl bromide is $BrRSO_2Br$.

4. The method of claim 2 wherein the reaction of the starting compound with the 1-haloalkyl 1-sulfonyl bromide is initiated by light.

5. The method of claim 2 wherein said reaction temperature is below 5° C.

6. The method of claim 2 wherein R is methylene.

7. The method of claim 1 wherein the aliphatic unsaturation begins at, at least, a $C_4$ carbon position or higher.

8. A method for the preparation of a conjugated aliphatically unsaturated compound which comprises the steps of preparing a first sulfone compound of the formula:

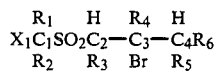

by reacting a second compound of the formula:

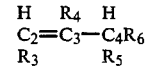

with a 1-haloalkyl 1-sulfonyl halide third compound of the formula:

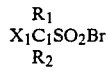

at a temperature below 25° C. for less than 12 hours in the absence of peroxide or metallic salt catalyst, wherein $X_1$ is independently chlorine, bromine or iodine and $R_1$ and $R_2$ are independently at each occurrence hydrogen, substituted or unsubstituted phenyl or alkyl where the substituents are halogen or alkoxy or additional $—SO_2Br$ groups; provided that each carbon atom of $R_1$ or $R_2$ which contains $—SO_2Br$ also contains an $X_1$ group and wherein $R_3$ through $R_6$ are independently at each occurrence $—OZ$, $—SiZ_3$, $—C_6M_5$, $—Z$ or $X_2$ where Z is hydrogen, substituted or unsubstituted phenyl, alkyl, alkenyl or alkynyl; $X_2$ is chlorine, bromine, iodine or fluorine; M is independently at each occurrence Z or $X_2$; $R_3$ and $R_4$ together may comprise an electron pair; two or more of $R_3$, $R_4$, $R_5$ and $R_6$ may be combined together and with one or more of $C_2$, $C_3$ or $C_4$ to form a ring structure; and $R_1$ nd $R_2$ may be joined together with $C_1$ to form a ring structure provided that none of $R_1$ through $R_6$ interfere with the reaction of the second and third compounds, and reacting the first sulfone compound with sufficient base for eliminating two hydrogens, $X_1$, Br and $SO_2$ to yield a compound with two conjugated nonaromatic carbon-carbon double bonds as a result of such elimination.

9. A method for the preparation of a conjugated aliphatically unsaturated compound which comprises the steps of preparing a first sulfone compound of the formula:

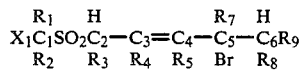

by reacting a second compound of the formula:

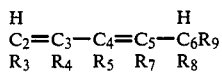

with a 1-haloalkyl 1-sulfonyl halide third compound of the formula:

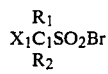

at a temperature below 25° C. for less than 12 hours, wherein $X_1$ is independently chlorine, bromine or iodine and $R_1$ and $R_2$ are independently at each occurrence hydrogen, substituted or unsubstituted phenyl or alkyl where the substituents are halogen or alkoxy or additional $-SO_2Br$ groups; provided that each carbon atom of $R_1$ or $R_2$ which contains $-SO_2Br$ also contains an $X_1$ group and wherein $R_3$ through $R_5$ and $R_7$ through $R_9$ are independently at each occurrence $-OZ$, $-SiZ_3$, $-C_6M_5$, $-Z$ or $X_2$, where Z is hydrogen, substituted or unsubstituted phenyl, alkyl, alkenyl or alkynyl; $X_2$ is fluorine, chlorine, bromine or iodine; M is independently at each occurrence Z or $X_2$; $R_3$ and $R_4$ together may comprise an electron pair; two or more of $R_3$, $R_4$, $R_5$, $R_7$, $R_8$ are $R_9$ may be joined together with one or more of $C_2$, $C_3$, $C_4$, $C_5$ or $C_6$ to form a ring structure; and $R_1$ and $R_2$ may be joined toether with $C_1$ to form a ring structure provided that none of $R_1$ through $R_5$ and $R_7$ through $R_9$ interfere with the reaction of the second and third compounds, and reacting the first sulfone compound with sufficient base for eliminating two hydrogens, $X_1$, Br and $SO_2$ to yield a compound with two additional conjugated nonaromatic carbon-carbon double bonds as a result of such elimination.

10. The method of claim 1 wherein the reaction product contains aliphatic unsaturation and yields a product containing three conjugated double bonds.

* * * * *

UNITED STATES PATENT AND TRADEMARK OFFICE
CERTIFICATE OF CORRECTION

PATENT NO. : 4,604,480

DATED : August 5, 1986

INVENTOR(S) : Eric Block and Mohammad Aslam

It is certified that error appears in the above-identified patent and that said Letters Patent is hereby corrected as shown below:

Column 18, line 10 "...$R_1$ through $R_5$ and ..." should read "...$R_1$ through $R_5$ or..."

Signed and Sealed this

Thirtieth Day of December, 1986

*Attest:*

DONALD J. QUIGG

*Attesting Officer*     *Commissioner of Patents and Trademarks*